ized Patent

(12) United States Patent
Brelvi et al.

(10) Patent No.: US 11,298,373 B1
(45) Date of Patent: Apr. 12, 2022

(54) BOWEL CLEANSING CHEMICAL COMPOSITION AND ASSOCIATED USE THEREFORE

(71) Applicants: Zamir Brelvi, Montville, NJ (US);
Kamal Dutta, Franklin Lake, NJ (US)

(72) Inventors: Zamir Brelvi, Montville, NJ (US);
Kamal Dutta, Franklin Lake, NJ (US)

(73) Assignee: Endologic LLC, Clifton, NJ (US)

( * ) Notice: Subject to any disclaimer, the term of this patent is extended or adjusted under 35 U.S.C. 154(b) by 52 days.

(21) Appl. No.: 16/721,688

(22) Filed: Dec. 19, 2019

Related U.S. Application Data

(60) Provisional application No. 62/782,485, filed on Dec. 20, 2018.

(51) Int. Cl.
*A61K 31/765* (2006.01)
*A61K 31/255* (2006.01)
*A61K 9/08* (2006.01)
*A61K 9/14* (2006.01)
*A61K 9/20* (2006.01)
*A61K 9/00* (2006.01)

(52) U.S. Cl.
CPC .............. *A61K 31/765* (2013.01); *A61K 9/08* (2013.01); *A61K 9/14* (2013.01); *A61K 9/20* (2013.01); *A61K 31/255* (2013.01); *A61K 9/0053* (2013.01)

(58) Field of Classification Search
CPC ...... A61K 31/765; A61K 31/255; A61K 9/14; A61K 9/20; A61K 9/0053
See application file for complete search history.

(56) References Cited

U.S. PATENT DOCUMENTS 9,040,095 B2    5/2015   Nizam

FOREIGN PATENT DOCUMENTS

CN          10365534       *  3/2014
WO          WO2009052256   *  4/2009

OTHER PUBLICATIONS

Wang, CN 103655534, published: Mar. 26, 2014, English machine translation obtained: Jun. 5, 2021. (Year: 2021).*
Ju Sung Sim and Ja Seol Koo, Predictors of Inadequate Bowel Preparation and Salvage Options on Colonoscopy, Clin Endosc 2016; 49:346-349, http://dx.doi.org/10.5946/ce.2016.094, Korean Society of Gastrointestinal Endoscopy, Korea.
Monique T. Barakat, MD, PHD, Robert J. Huang, MD, Subhas Banerjee, MD, Simethicone is retained in endoscopes despite reprocessing: impact of its use on working channel fluid retention and adenosine triphosphate bioluminescence values (with video), Gastrointest Endosc 2019; 89:115-23, United States.
Olympus, Olympus letter to health care providers, Jun. 29, 2018. Use of simethicone and other non-water soluble additives with Olympus flexible endoscope, United States.
Edwin J. Lai, MD, Audrey H. Calderwood, MD, Gheorghe Doros, PHD, Oren K. Fix, MD, MSC, and Brian C. Jacobson, MD, MPH, Fasge, The Boston Bowel Preparation Scale: A valid and reliable instrument for colonoscopy-oriented research, Gastrointest Endosc. 2009; 69(3 Pt 2): 620-625, http://dx.doi.org:10.1016/j.gie.2008.05.057, United States.
Andrew R. Kelleher, PHD, MS, FDA minutes from Type C meeting on GutRinse. Nov. 29, 2018, United States.

* cited by examiner

*Primary Examiner* — Genevieve S Alley
(74) *Attorney, Agent, or Firm* — Ashkan Najafi

(57) ABSTRACT

A GRAS list chemical composition (containing only GRAS list approved ingredients) including a water-based bowel cleansing solution (either in concentrate form or diluted form) to clean a gastrointestinal (GI) tract before and/or during performance of an endoscopy procedure such as a colonoscopy, enteroscopy, upper gastrointestinal endoscopy, and small bowel capsule endoscopy, for example. The GRAS list bowel cleansing chemical composition includes at least one of a chemical composition as a liquid, tablet or powder concentrate that can be added to sterile water or other solution by the end-user to make the chemical composition solution; and a pre-mixed chemical composition solution diluted in up to 1000 ml of sterile water.

9 Claims, 1 Drawing Sheet

GRAS List Bowel Cleansing Chemical Composition

Sterile water: about 94% to 99%; or as allowed by the FDA

PEG 3350: about 3%, 30g; 6%, 60g; 1.5%, 15g; or as allowed by FDA

Sodium Docusate: preferably about .048%, 480 mg/liter, with a range of about 50 mg to 500 mg, the maximum dose per day per the US FDA GRAS list, as allowed by FDA Simethicone: preferably about .048%, about 480 mg/liter, with a range of about 50 mg to 3000 mg/ 100 ml, or 3% or a level that has been shown to form residual droplets in the working channel of endoscopes and as allowed by FDA. Another preferred embodiment of a safe and effective quantity of simethicone = about 100mg/100ml or about 0.1% of simethicone.

BOWEL CLEANSING CHEMICAL COMPOSITION AND ASSOCIATED USE THEREFORE

CROSS REFERENCE TO RELATED APPLICATIONS

This is a non-provisional patent application that claims the benefit of U.S. provisional patent application No. 62/782,485 filed Dec. 20, 2018, which is incorporated by reference herein in its entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

Technical Field

Exemplary embodiment(s) of the present disclosure relate to bowel cleansing chemical compositions and, more particularly, to a GRAS list chemical composition (containing only GRAS list approved ingredients) including a water-based bowel cleansing solution (either in concentrate form or diluted form) to clean a gastrointestinal (GI) tract before and/or during performance of an endoscopy procedure such as a colonoscopy, upper gastrointestinal endoscopy, and small bowel capsule endoscopy, for example.

Prior Art

Approximately, 30 million colonoscopy, 10 million upper gastrointestinal endoscopy and 1 million small bowel capsule endoscopy procedures are performed annually in the US. Colonoscopy procedures are performed predominantly to screen both men and women for bowel cancer. Fifty million US residents are eligible for bowel cancer screening.

In a non-limiting example, colonoscopy is a procedure whereby a fiber-optic instrument is introduced into the rectum via the anal canal. The leading end of the instrument is gradually advanced all the way up to the cecum, e.g., the beginning of the bowel. When the leading end of the instrument is in the cecum, the actual examination starts. If the cecum is spotlessly clean, its surface is examined in detail for any abnormality, like a growth or a tumor (usually called a polyp). The instrument is then gradually withdrawn through the entire length of the bowel. The surface of the bowel is washed with water to remove any adherent stool or secretions to assist with detailed examination. This extra cleansing can be undertaken before or during the colonoscopy to avoid missing any small or "flat growth. Despite best efforts for cleansing the bowel prior to doing a colonoscopy, there is always some residual stool and secretions in the bowel, which pose a hindrance in visualization and careful examination of the surface of the bowel.

The prevailing practice is generally to wash the residual stool and secretions with water. The water is introduced into the bowel by either injecting it down the working channel of the instrument (e.g. the colonoscope or by means of a pump with a foot pedal). The water source is connected to the colonoscope by a tube and water can be introduced into the bowel by pushing the foot pedal.

In another non-limiting example, an upper gastrointestinal endoscopy (i.e., Esophagus-Gastro-Duodenoscopy, EGD) is performed predominantly to evaluate epigastric pain and suspected gastrointestinal bleeding from gastric ulcers.

In yet another non-limiting example, a small bowel capsule endoscopy procedure is performed to look for small bowel bleeding in patients that have not shown active bleeding in the upper gastrointestinal tract or bowel.

A key feature of each aforementioned procedure requires being able to visualize the lining of the gastrointestinal tract to enable a high-quality examination. Before undergoing these procedures, the patients are prepared to allow for a high-quality examination of the gastrointestinal tract.

In a non-limiting example, prior to a colonoscopy, the patient is required to consume a clear liquid diet the day before the procedure and consume a "cleansing" solution or tablets to clean the bowel. A variety of bowel cleansing preparations are available to clean the bowel before the colonoscopy procedure. In clinical trials, the bowel cleansing preparation has shown to be effective. In clinical practice, about 25% of patients have an inadequate bowel preparation making their exam suboptimal (1) Due to the suboptimal exam, these patients are required to come back for a repeat bowel exam before the recommended guideline. Suboptimal bowel preparations add a significant cost to our healthcare resources.

In another non-limiting example, prior to performing an upper endoscopy, the patient fasts for about 12 hours allowing the stomach contents to pass-through to the small intestine. Due to underlying motility problems, some patients do not have a clean stomach thereby making the exam suboptimal. Some patients also have a suboptimal exam due to blood in the stomach. Some patients have copious amounts of foam also making the upper endoscopy exam inadequate.

In yet another non-limiting example, prior to performing a small bowel capsule endoscopy, patients are required to drink between 500 ml to 1 liter of a conventional bowel cleansing solution to clean the small bowel. A majority of small intestinal capsule endoscopy exams are suboptimal due to the presence of foam and froth caused by bile salts in the small intestine. To improve the quality of the exam, some medical providers use simethicone, which is an anti-foaming agent used to reduce bloating caused by excessive gas.

During a colonoscopy or an upper endoscopy if the preparation is suboptimal, the bowel or upper gastrointestinal tract is rinsed with water, which is injected through an irrigation channel of the endoscope. During a small bowel capsule procedure, since it is performed indirectly, there is no cleansing option and a suboptimal preparation leads to a suboptimal exam.

With conventional practices, water is often used to clean the gastrointestinal tract during the endoscopic procedures. Some endoscopists add simethicone in the form of infant gas relief formulations that are commercially available to aid as a defoaming agent to the water that is used during endoscopy.

To prepare for small bowel capsule endoscopy, polyethylene glycol (PEG) based bowel prep solutions are used the day before the procedure.

Although conventional methods employ water for cleansing during a colonoscopy or EGD, it is not ideal. Stool present during a colonoscopy is often adherent and sticky. Using water in these circumstances is ineffective and leads to more foaming that further obstructs the view and making the exam worse. Similarly, during an EGD, food residue and blood cannot be cleaned adequately with water.

U.S. Pat. No. 9,040,095 to Nizam discloses a bowel cleansing chemical composition that includes PEG 3350, simethicone, and, N. Acetyl Cysteine (NAC), which is not safe because NAC is not on the US FDA's Generally Recognized as Safe (GRAS) list.

Accordingly, a need remains for a more effective and safer bowel cleansing solution that contains only GRAS list approved ingredients, other than water, for use before and/or during colonoscopy, EGD, and small bowel capsule endoscopy procedures. The non-limiting exemplary embodiment(s) of the present disclosure satisfy such a need, and may be referred to generally as GUT-RINSE™ here in below.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a bowel cleansing chemical composition for cleansing a bowel of a patient during an endoscopy procedure. These and other objects, features, and advantages of the non-limiting exemplary embodiment(s) are provided by a chemical composition including a plurality of GRAS list ingredients including: a safe and effective quantity of sterile water equal to less than 99 percent weight/volume; a safe and effective quantity of PEG 3350 equal to about 6 percent weight/volume; a safe and effective quantity of sodium docusate equal to about 0.048 percent weight/volume; and a safe and effective quantity of simethicone equal to about 0.048 percent weight/volume.

In a non-limiting exemplary embodiment, the chemical composition is a homogenous concentrated liquid solution.

In a non-limiting exemplary embodiment, the chemical composition is a homogenous diluted pre-mixed liquid solution.

In a non-limiting exemplary embodiment, the chemical composition is a powder or tablet.

The present disclosure further includes a method of utilizing a bowel cleansing chemical composition for cleansing a bowel of a patient during an endoscopy procedure. Such a method includes the steps of: providing a plurality of GRAS list ingredients including a safe and effective quantity of sterile water equal to less than 99 percent weight/volume; a safe and effective quantity of PEG 3350 equal to about 6 percent weight/volume; a safe and effective quantity of sodium docusate equal to about 0.048 percent weight/volume; and a safe and effective quantity of simethicone equal to about 0.048 percent weight/volume; and applying the chemical composition to a bowel target area.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 1 is a block diagram illustrating the ingredients of the GRAS List Bowel Cleansing chemical composition, in accordance with a non-limiting exemplary embodiment of the present disclosure.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

If used herein, "about" means approximately or nearly and in the context of a numerical value or range set forth means±15% of the numerical.

If used herein, "substantially" means largely if not wholly that which is specified but so close that the difference is insignificant.

A non-limiting exemplary embodiment(s) of the present disclosure is referred to generally in FIG. 1 and is intended to provide a chemical composition 10 (containing only GRAS list approved ingredients) including a water-based bowel cleansing solution (either in concentrate form or diluted form) to clean a gastrointestinal (GI) tract before and/or during performance of an endoscopy procedure such as a colonoscopy, upper gastrointestinal endoscopy, and small bowel capsule endoscopy, for example. It should be understood that the exemplary embodiment(s) may be used with a variety of endoscopic procedures, and should not be limited to any particular endoscopic procedure described herein. As noted hereinabove, the GRAS list bowel cleansing chemical composition 10 may be referred to generally as GUT-RINSE™ or GUTRINSE™ here in below.

Non-limiting exemplary advantages of the GRAS list bowel cleansing chemical composition 10 (GUTRINSE™) include, inter alia, the following: 1. Contains standard quantities of GRAS listed chemicals that improve on ability of water to clean the GI tract which is currently the standard of care. 2. Does not allow the simethicone to adhere to the inner wall of the working channel of the endoscope. Previous research studies have shown that Simethicone in a concentration above 0.5% will adhere to the working channel as residual droplets of a gastroscope and colonoscope. See non-patent literature submitted in Applicants' IDS. The concentration of Simethicone will be below the concentration that form residual droplets in the working channel. 3. Has simethicone without the sugar, that is currently used in the form of infant gas relief formulation that causes greater adherence of simethicone to the inner wall of the working channel of endoscopes thereby promoting bacterial growth in the sugar rich Simethicone. 4. Can be added to the PEG based cleaning solution or diluted in water for use for preparation before small bowel capsule endoscopy to have a better-quality preparation without the foam.

Referring generally to the block diagram in FIG. 1, in non-limiting exemplary embodiment(s), the GRAS list chemical composition 10 is a novel and useful bowel cleansing solution that performs better than the current state of art, (e.g., water). The present GRAS list bowel cleansing chemical composition 10 is a safe and better alternative to water to clean the gastrointestinal (GI) tract during an endoscopic procedure. The GRAS list bowel cleansing chemical composition 10 includes three exemplary ingredients including: polyethylene glycol (PEG 3350), sodium docusate, and simethicone. In particular, the GRAS list bowel cleansing chemical composition 10 is effective in cleansing the bowel during a colonoscopy procedure, while reducing foaming as the bowel is cleansed.

Advantageously, all components (e.g., ingredients) of the GRAS list bowel cleansing chemical composition 10 are listed on the Generally Regarded As Safe (GRAS) list published by the US FDA. Besides water, the exemplary above-described components are within the daily limit allowed by the US FDA up to one liter of the chemical composition 10 utilized for the aforementioned endoscopic procedures. The approval process for GUTRINSE™ is currently on going with discussions with the FDA and a 505(b2) pathway for a New Drug Application (NDA) for GUTRINSE has been recommended by the FDA (5).

In a non-limiting exemplary embodiment, the combination of GRAS list ingredients includes the following: (1) PEG 3350 (bowel cleansing ingredient); (2) sodium docusate (surfactant and known stool softener that allows for better cleansing of the gastrointestinal tract particularly the bowel to remove adherent stool and residue); and (3) simethicone (eliminates foam and froth formed while cleansing the bowel with plain water).

In a non-limiting exemplary embodiment, the GRAS list bowel cleansing chemical composition 10 can be provided, for example, in powder form to maximize shelf life and enable the mixture to be prepared when it is needed.

In a non-limiting exemplary embodiment, the GRAS list bowel cleansing chemical composition 10 can be mixed into a water-based solution form with added saline or other flavored electrolyte solutions In a non-limiting exemplary embodiment, the GRAS list bowel cleansing chemical composition 10 can be, for example, readily soluble, and thus reconstitution generally requires normal mixing.

In a non-limiting exemplary embodiment, the GRAS list bowel cleansing chemical composition 10 can be kept in liquid form.

In a non-limiting exemplary embodiment, the GRAS list bowel cleansing chemical composition 10 can be provided as a concentrate for dilution, as a working strength preparation of individual components for later combination, or in solid or liquid oral dosage forms.

In a non-limiting exemplary embodiment, the GRAS list bowel cleansing chemical composition 10 in powder or tablet form can be packaged in, for example, a transparent plastic container, and can be, for example, transparent. Other packaging materials can also be used, as would be understood by a person of ordinary skill in the art.

In a non-limiting exemplary embodiment, the compounds of the present disclosure are useful as GRAS list pharmaceutical chemical composition 10 prepared with a therapeutically effective amount of a compound, as defined herein, and a pharmaceutically acceptable carrier or diluent.

In non-limiting exemplary embodiments, the GRAS list bowel cleansing chemical composition 10 may be in concentrated liquid and/or powder forms. For example, the GRAS list bowel cleansing chemical composition 10 may be provided in the following forms: (1) a chemical composition 10 as a liquid or powder concentrate that can be added to sterile water by the end-user to make the chemical composition 10 solution; and (2) a pre-mixed chemical composition 10 solution diluted in 250 ml, 500 ml or 1000 ml of sterile water.

In a non-limiting exemplary embodiment, the GRAS list bowel cleansing chemical composition 10 includes water as the main cleansing component. The additional components of GRAS list bowel cleansing chemical composition 10 provide the following added benefits: (1) polyethylene glycol 3350 (PEG) is a safe bowel cleanser, it is not absorbed by the gastrointestinal tract. Addition of PEG to the GRAS list bowel cleansing chemical composition 10 and allows for improved cleaning of the stool and residue when the solution when used directly on the target. (2) Sodium docusate is a safe stool softener. It reduces the surface tension of the stool and residue and makes it less adherent. Using sodium docusate provides easy removal of stool and residue from the wall of the gastrointestinal tract. (3) Simethicone is a safe defoaming chemical that eliminates foam or froth formed during bowel cleansing.

It is noted that water is the most common component that is employed for bowel cleansing during a colonoscopy and EGD. PEG-based bowel cleansing solutions are used to prepare patients before a small bowel capsule endoscopy. However, none of the PEG based solution have a defoaming chemical to prevent the foam formation in the small bowel. The GRAS list bowel cleansing chemical composition 10 offers safe and more effective cleansing of the gastrointestinal tract than water. In addition, its unique composition allows more effective upper, small bowel and colon cleansing. In addition, it has a defoaming capability; water does not have this.

It is noted that some conventional bowel cleansing solutions add a defoaming feature to water. For example, many endoscopists add variable amounts (1 ml to 20 ml) of infant gas relief preparations of simethicone. This practice of adding gas relief solution to water during endoscopic procedures has come under question and discouraged. Major endoscope manufactures have issued notices and have recommended against the use of infant gas relief preparations with Simethicone during endoscopic procedures. See non-patent literature submitted in Applicants' IDS. Reported research studies demonstrating the residual droplet formation in the working channel of endoscopes despite High Level Disinfection HLD) cleaning of the endoscope. See non-patent literature submitted in Applicants' IDS Hence, addition of a gas relief solution that has high amounts of sugar (to make it palatable for infants) may be a potential infection risk for patients because the sugar-containing simethicone solution cannot be removed adequately even with High Level Disinfection (HLD) endoscope cleansing methods, thereby may allow growth of harmful bacteria. Advantageously, the GRAS list bowel cleansing chemical composition 10 has simethicone without sugar and in a concentration below the level that has been to cause residual droplets in the working channel of endoscopes. Also, the GRAS list bowel cleansing chemical composition 10 offers a uniform amount of simethicone within the established safety limits approved by the FDA. Furthermore, the GRAS list bowel cleansing chemical composition 10 reduces the surface tension of stool and residue attached to the gastrointestinal tract; sterile water is less effective in doing this.

In a non-limiting exemplary embodiment, the one liter of the GRAS list bowel cleansing chemical composition 10 (GUT-RINSE™) is a water-based solution that preferably includes the following ingredients (percent weight/volume (% w/v)):

1. a safe and effective quantity of sterile water=preferably about 94% to 99% as allowed by the FDA.

2. a safe and effective quantity of PEG 3350=preferably about 6% or 60 g, 3% or 30 g, 1.5% or 15 g as allowed by the FDA.

3. a safe and effective quantity of sodium docusate=preferably about 0.048%, about 480 mg/liter, with a range of about 50 mg to 500 mg, the maximum dose allowable per day per the US FDA GRAS list; as allowed by the FDA.

4. a safe and effective quantity of simethicone=preferably about 0.048%, about 480 mg/liter, with a range of about 50 mg to 3000 mg/100 ml or 3% or a level that has been shown to form residual droplets in the working channel of endoscopes and as allowed by the FDA. Another preferred embodiment of a safe and effective quantity of simethicone=about 100 mg/100 ml or about 0.1% of simethicone.

In a non-limiting exemplary embodiment, the GRAS list bowel cleansing chemical composition 10 may be employed as follows: (1) cleaning of the GI tract (especially bowel) during a upper endoscopy, enteroscopy and colonoscopy procedure, maximum amount to be used is preferably 1 liter; and (2) cleaning of the small intestine before a small bowel capsule endoscopy procedure, preferably use 500 ml up to one liter for this procedure.

In a non-limiting exemplary embodiment, the GRAS list bowel cleansing chemical composition 10 is a homogenous concentrated liquid solution.

In a non-limiting exemplary embodiment, the GRAS list bowel cleansing chemical composition 10 is a homogenous diluted pre-mixed liquid solution.

In a non-limiting exemplary embodiment, the GRAS list bowel cleansing chemical composition 10 is a powder.

Example 1

In a non-limiting exemplary embodiment, the GRAS list bowel cleansing chemical composition 10 may be employed in the following scenario. A patient with an average risk for colon cancer comes for a colonoscopy for colon cancer screening. An endoscopist performs the colonoscopy. The left and middle segments (rectum, sigmoid bowel, descending bowel and transverse bowel) of the bowel is adequately cleaned with good visualization of the bowel. However, the right segment (ascending bowel and cecum) cannot be visualized due to thick dark adherent stool lining the walls of the bowel. The endoscopist washes the wall with water using an irrigation pump. Some of the sticky stool comes off the wall but now the lumen of the bowel is filled with a foam as a result of the washing. The water-stool mixture can be suctioned off, but the foam persists. The endoscopist uses the GRAS list bowel cleansing chemical composition 10 to wash the bowel with the irrigation pump. The GRAS list bowel cleansing chemical composition 10 eliminates the foam (since it contains simethicone, a defoaming chemical). In addition, the sticky adherent stool also comes off the wall easily due to the PEG 3350 (increases density of the solution). Also, the sodium docusate, a surfactant (reduces surface tension of stool). The resulting stool mixture can be suctioned off leaving behind clearly visible bowel wall. When water is used during the colonoscopy procedure, the bowel preparation will be rated as inadequate and will have to be repeated in 1 year. A widely used bowel preparation scoring system is the Boston Bowel Prep Scoring System (BPSS). A score using the BPSS of 5 and less is considered inadequate with a recommendation to repeat within 1 year (4). Using the GRAS list bowel cleansing chemical composition 10 of the present disclosure, the bowel preparation will be rated as "fair" or "good" and the repeat colonoscopy will be recommended in 3 or 5 years thereby reducing cost, time and resources.

Example 2

In a non-limiting exemplary embodiment, the GRAS list bowel cleansing chemical composition 10 may be employed in the following scenario. A patient with a history of bowel polyps comes for a colonoscopy. The entire bowel is clean with no stool on the wall of the bowel. However, in the cecum there is a dark liquid (bile). The endoscopist irrigates with water to suction the liquid. The entire cecum fills up with yellow foam and makes the visualization of the cecum worse. The endoscopist uses the GRAS list bowel cleansing chemical composition 10 to irrigate and suction. The cecum is now clearly visible, and the foam has dissipated. The endoscopist notes a broad-based polyp in the cecum. The polyp is sent for analysis. The pathology report states that it is an adenomatous polyp with early bowel cancer. Using water to clean the bowel in this patient would have resulted in a missed polyp leading to bowel cancer in the future. The use of the GRAS list bowel cleansing chemical composition 10 allowed for better polyp detection and saved this patient from bowel cancer.

Example 3

In a non-limiting exemplary embodiment, the GRAS list bowel cleansing chemical composition 10 may be employed in the following scenario. A patient is admitted to the hospital with abdominal pain, anemia and black tarry stools. The gastroenterologist suspects a bleeding ulcer. An upper endoscopy is performed. The stomach shows "coffee ground" like material indicating oxidized blood. The stomach does not show any ulcers. The duodenum is approached but there is a bile and blood mixture. The endoscopist uses water to clean and suction, however the situation gets worse due to the foam, now the wall of the duodenum is not visible where the ulcer is suspected and is bleeding. The endoscopist uses the GRAS list bowel cleansing chemical composition 10 to clean the area, the foam disappears and a duodenal ulcer with a visible blood vessel is seen. Since the area is now clearly visible, the endoscopist treats the ulcer with cautery and injection and stops it from bleeding again. The patient is discharged in two days on medication. A repeat upper endoscopy is performed in eight weeks and the ulcer is healed. If the ulcer bleeding could not be stopped, the patient would have needed more blood transfusion, longer stay in the intensive care unit (ICU) and surgical treatment for the ulcer.

In a non-limiting exemplary embodiment, the amount of the GRAS list bowel cleansing chemical composition 10 required for use in treatment may vary with the route of administration, the nature of the condition being treated and the age and condition of the patient and will be ultimately at the discretion of the medical practitioner.

In a non-limiting exemplary embodiment, effective dosages of the GRAS list bowel cleansing chemical composition 10 may vary from patient to patient, depending on, for example, the sex, age, weight, and general or clinical condition of the patient, the severity or mechanism of any disorder being treated, the particular vehicle used, the method and scheduling of administration, and the like.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A bowel cleansing chemical composition, said chemical composition comprising: a plurality of GRAS list ingredients including
    a safe and effective quantity of sterile water;
    a safe and effective quantity of PEG 3350 equal to about 1.5 to 6 percent weight/volume;
    a safe and effective quantity of sodium docusate equal to about 0.048 percent weight/volume; and
    a safe and effective quantity of simethicone equal to about 0.048 to 3 percent weight/volume.

2. The chemical composition of claim 1, wherein said chemical composition is a homogenous concentrated liquid solution.

3. The chemical composition of claim 1, wherein said chemical composition is a homogenous diluted pre-mixed liquid solution.

4. A bowel cleansing chemical composition for cleansing a bowel of a patient, said chemical composition comprising:
a plurality of GRAS list ingredients including
    a safe and effective quantity of sterile water equal to less than 99 percent weight/volume;
    a safe and effective quantity of PEG 3350 equal to about 1.5 to 6 percent weight/volume;
    a safe and effective quantity of sodium docusate equal to about 0.048 percent weight/volume; and
    a safe and effective quantity of simethicone equal to about 0.048 to 3 percent weight/volume.

5. The chemical composition of claim 4, wherein said chemical composition is a homogenous concentrated liquid solution.

6. The chemical composition of claim 4, wherein said chemical composition is a homogenous diluted pre-mixed liquid solution.

7. A method of utilizing a bowel cleansing chemical composition for cleansing a bowel of a patient, said method comprising the steps of:
   providing a plurality of GRAS list ingredients including a safe and effective quantity of sterile water equal to less than 99 percent weight/volume; a safe and effective quantity of PEG 3350 equal to about 1.5 to 6 percent weight/volume; a safe and effective quantity of sodium docusate equal to about 0.048 percent weight/volume; and a safe and effective quantity of simethicone equal to about 0.048 to 3 percent weight/volume; and
   applying the chemical composition to a bowel target area during an endoscopy or colonoscopy procedure.

8. The method of claim 7, wherein said chemical composition is a homogenous concentrated liquid solution.

9. The method of claim 7, wherein said chemical composition is a homogenous diluted pre-mixed liquid solution.

\* \* \* \* \*